(12) United States Patent
Dankers et al.

(10) Patent No.: US 10,905,796 B2
(45) Date of Patent: Feb. 2, 2021

(54) SUPRAMOLECULAR POLYMER BLEND

(71) Applicant: TECHNISCHE UNIVERITEIT EINDHOVEN, Eindhoven (NL)

(72) Inventors: Patricia Dankers, Eindhoven (NL); Björne Mollet, Eindhoven (NL); Samaneh Kheyrrooz, Eindhoven (NL); Bastiaan Ippel, Eindhoven (NL); Henk Keizer, Eindhoven (NL); Geert Van Almen, Eindhoven (NL); Frank Baaijens, Eindhoven (NL)

(73) Assignees: Xeltis AG, Zurich (CH); Technische Universiteit Eindhoven, Eindhoven (NL)

( * ) Notice: Subject to any disclaimer, the term of this patent is extended or adjusted under 35 U.S.C. 154(b) by 15 days.

(21) Appl. No.: 15/544,468

(22) PCT Filed: Jan. 29, 2016

(86) PCT No.: PCT/EP2016/051943
§ 371 (c)(1),
(2) Date: Jul. 18, 2017

(87) PCT Pub. No.: WO2016/120456
PCT Pub. Date: Aug. 4, 2016

(65) Prior Publication Data
US 2018/0015202 A1  Jan. 18, 2018

(30) Foreign Application Priority Data

Jan. 30, 2015 (EP) .................................... 15153251

(51) Int. Cl.
A61L 27/26 (2006.01)
A61L 27/50 (2006.01)
C08G 18/73 (2006.01)
C08G 18/42 (2006.01)
C08G 71/02 (2006.01)
A61L 33/06 (2006.01)
C08L 67/04 (2006.01)

(52) U.S. Cl.
CPC ............ A61L 27/26 (2013.01); A61L 27/507 (2013.01); A61L 33/062 (2013.01); C08G 18/4244 (2013.01); C08G 18/73 (2013.01); C08G 71/02 (2013.01); C08L 67/04 (2013.01)

(58) Field of Classification Search
CPC ....................................................... A61L 27/26
See application file for complete search history.

(56) References Cited

U.S. PATENT DOCUMENTS

| 2008/0262618 | A1* | 10/2008 | Hermsen | ............... | A61F 2/3872 |
| | | | | | 623/14.12 |
| 2012/0148500 | A1* | 6/2012 | Brizard | ............... | A61K 49/126 |
| | | | | | 424/9.37 |

FOREIGN PATENT DOCUMENTS

EP  2468305  6/2012

OTHER PUBLICATIONS

Koenings et al. Tuning Cross-Link Density in a Physical Hydrogel by Supramolecular Self-Sorting. Macromolecules 2014, 47:2712-2717.
Mollet et al. A modular approavh to easily processable supramolecular bilayered scaffold with tailorable properties. J. Materials Chemistry B 2(17) 2483-2493.
Ramaekers. PhD thesis Jan. 1, 2015. Supramolecular biomaterials based on ureido-pyrimidinones and cucurbiturils Eindhoven: Technische Universiteit Eindhoven https://pure.tue.nl/ws/portalfiles/portal/3789711/797270.pdf.

* cited by examiner

Primary Examiner — Michael F Pepitone
(74) Attorney, Agent, or Firm — Lumen Patent Firm

(57) ABSTRACT

A supramolecular polymer blend includes a thermoplastic elastomer functionalized with at least one bis-urea moiety and a functional component which is functionalized with at least one bis-urea moiety which is present in an amount of 0.5-40 wt % based on the total mass of the polymer blend. The functional component is selected from polyalkylene glycol, betaine, polysaccharide, zwitterion, polyol or taurine and derivatives thereof. Implants including the polymer blend and a process to manufacture the implants are also provided.

17 Claims, 7 Drawing Sheets

FIG. 3A-1
A : P
3 hours after seeding
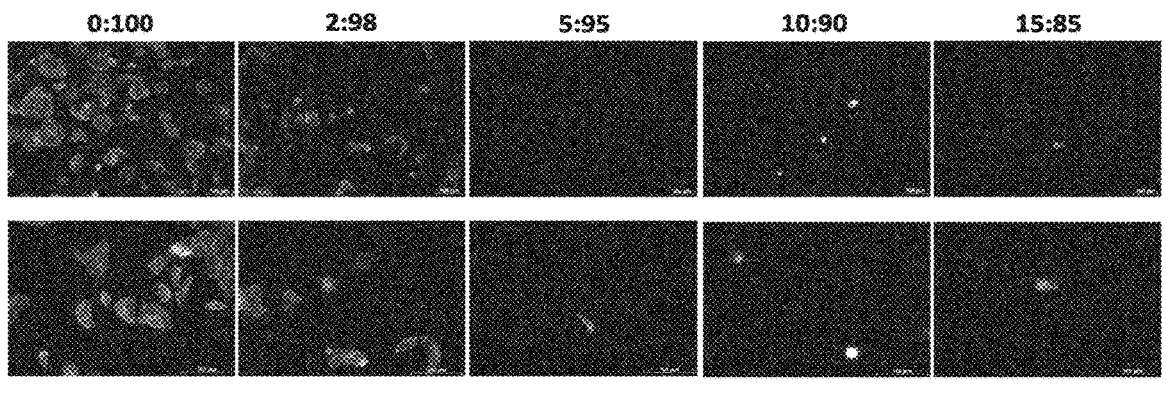
FIG. 3A-2
B : P
3 hours after seeding
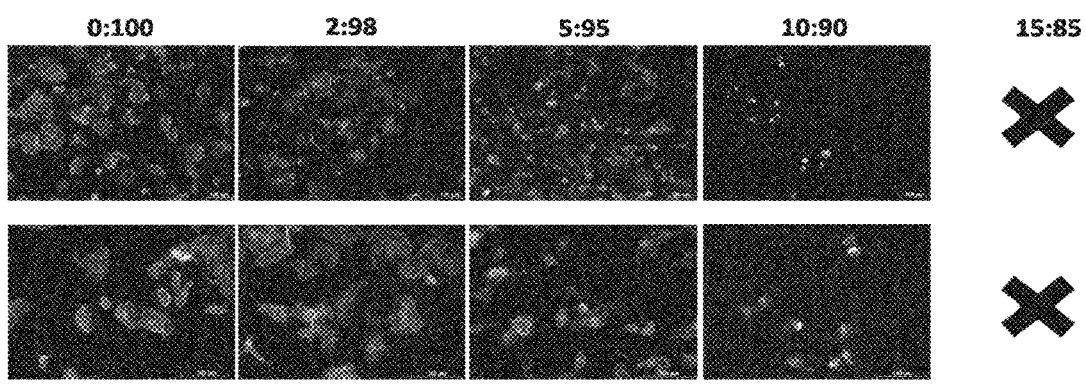

72 hours

Glass

P

| | 2:98 | 10:90 | | 2:98 | 10:90 |
|---|---|---|---|---|---|
| I:P |  |  | A:P |  |  |
| 1:P |  |  | A':P |  |  |
| 2:P |  |  | B:P |  |  |
| 3:P |  |  | B':P |  |  |

SUPRAMOLECULAR POLYMER BLEND

CROSS-REFERENCE TO RELATED APPLICATIONS

This application is a 371 of PCT Patent Application PCT/EP2016/051943 filed Jan. 29, 2016. PCT/EP2016/051943 claims the benefit of EP Application 15153251.2 filed Jan. 30, 2015.

BACKGROUND

Described herein is a supramolecular polymer blend comprising a thermoplastic elastomer functionalized with at least one bis-urea moiety and a functional component which is also functionalized with at least bis-urea moiety and in which the functional component is present in an amount of 0.5-40 wt % based on the total mass of the polymer blend, to implants comprising said supramolecular polymer blend, and to a process to manufacture implants from said supramolecular polymer blend.

Conventional polymers, as e.g. polytetrafluoroethylene, and supramolecular thermoplastic elastomers—sometimes in combination with various functional molecules—have been tested for use in prosthetics and grafts.

The currently used devices have some disadvantages. For example, AV grafts may be used for vascular access necessary for hemodialysis only several weeks after implantation. An arteriovenous (AV) graft is created by connecting a vein to an artery using a soft plastic tube. After the graft has healed, hemodialysis may be performed. Currently used AV grafts are primarily composed of non-degradable polytetrafluoroethylene (PTFE).

Also known is the use of electro-spun polycarbonate urethane materials for AV shunts which may be used for vascular access within 48 hours. However, the primary mode of failure of these grafts was the occurrence of thrombosis (Karatepe et al., J Vasc Access. 2013 Oct. 1; 14(3):273-80).

Therefore, there is a need for biomaterials which overcome the disadvantages of the prior art and which may be used for AV grafts but also for other in vivo uses where implants, such as vascular grafts, heart valves and vascular valves, are in contact with bodily fluids, more specifically blood.

Supramolecular thermoplastic elastomers and blends or composites comprising these polymers are known and have been described for various applications, including biomedical applications, more specifically regenerative medicine.

Supramolecular polymers are polymers that are usually of lower molecular mass and (self-) assemble into polymers of a higher virtual molecular mass and show the behavior of such higher molecular mass polymers. The supramolecular polymers usually assemble via non-covalent bonding, e.g. via hydrogen bonds. Via non-covalent bonding also other functional compounds or fillers can be incorporated into the assembly.

Wisse et al. (Macromolecules 2006, 39, 7425-7432) describe how supramolecular fillers are incorporated into a bisurea functionalized polycaprolactone-based supramolecular polymer and how the mechanical properties of the polycaprolactone-based polymer (the base polymer) may be tuned. Wisse does not disclose how the filler can influence the biofunctional properties of the base polymer and what blends are suited for use in prosthetics and grafts.

US2008/0262618 A1 refers to prosthetic devices for use in the joint space between bones formed from supramolecular polymers comprising a thermoplastic elastomer which may comprise bis-urea units and a functional component. The functional component may also include bis-urea units and can be selected from a dye or peptide and is added to the base polymer to stimulate cell adhesion, induce chondrocyte differentiation and to improve the mechanical properties of the new cartilage.

WO2014/007631 A1 discloses an implant comprising a matrix material including at least one supramolecular compound, e.g. bis-urea modified polycaprolactone (PCL-bisurea). The matrix material may further comprise biologically active compounds or contrast agents. The biologically active compounds have not been further specified.

Dankers et al. (Nature Materials, Vol. 4, July 2005, p. 568-574) discloses blends of ureido-pyrimidinone (UPy)-modified oligocaprolactones and UPy-modified peptides. Bis-urea modified thermoplastic elastomers are not disclosed and the blends do not have antifouling properties.

Wisse et al. (Biomacromolecules, 7, 2006, p. 3385-3395) discloses blends of bisurea-modified oligocaprolactones and a bisurea-modified GRGDS peptide. Also this blend does not have antifouling properties.

Even though biomaterials comprising bis-urea modified supramolecular base polymers are known, biomaterials comprising supramolecular base polymers with anti-fouling, anti-thrombogenic and/or non-cell-adhesive properties have not been disclosed.

Such supramolecular polymer blends are especially suited for use in vivo in blood-contacting devices, including e.g. cardiovascular devices as vascular grafts, cardiac patches, AV (arteriovenous) shunts or cardiac valves.

Further, here is a general need for alternative and improved biomaterials.

BRIEF SUMMARY

The present disclosure provides such materials.

The polymer blend of the present disclosure is a biomaterial with improved anti-fouling and non-cell-adhesive properties. In one embodiment it may also have anti-thrombogenic properties.

The supramolecular polymer blend comprises a thermoplastic elastomer functionalized with at least one bis-urea moiety and a functional component, which is functionalized with at least one bis-urea moiety which is present in an amount of 0.5-40 wt % based on the total mass of the polymer blend, wherein the functional component is selected from a group consisting of polyalkylene glycol, betaine, polysaccharide, polyols, a zwitterion or taurine or derivatives thereof.

The functional component (also called additive) is a bis-urea functionalized, i.e. bis-urea-modified molecule, an oligomer or low molecular weight polymer, which interacts with the thermoplastic elastomer.

BRIEF DESCRIPTION OF THE DRAWINGS

FIGS. 3A-1, 3A-2, 3B-1, 3B-2, 3C-1 and 3C-2 show the cell adhesion behavior of HK2 cells at different times after seeding on different surfaces.

DETAILED DESCRIPTION

Figure 1:
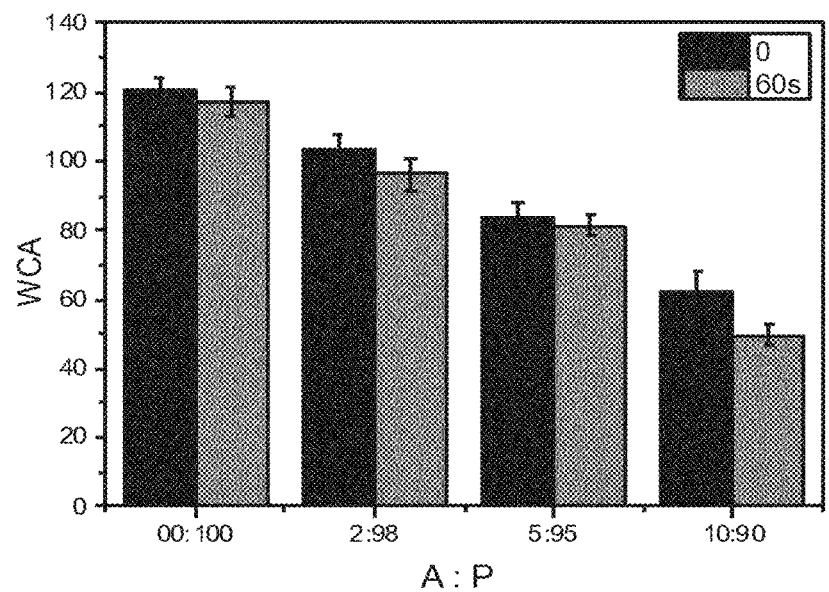
FIG. 1 shows the water contact angle of different supramolecular polymer blends according to the disclosure.
Figure 1:
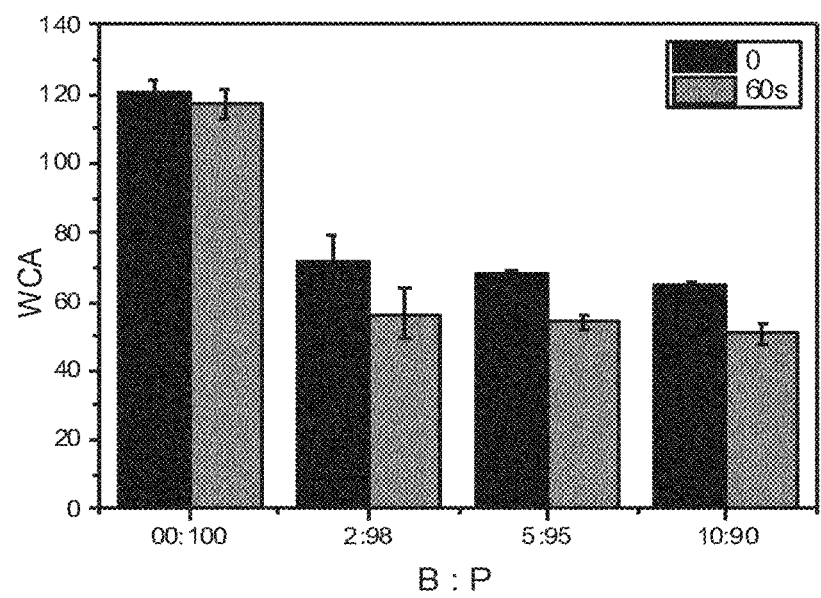

In one embodiment, where the functional component (also referred to as additive) is a polyalkylene glycol, it is a bis-urea functionalized poly- or oligoethylene glycol (PEG, OEG).

Polyethylene glycol refers to an ethylene glycol compound with an average molecular weight of above 20000 g/mole, while oligoethylene glycol refers to an ethylene glycol compound with an average molecular weight of below 20000 g/mol.

In an embodiment the functional component is a molecule which comprises a bis-urea moiety where the urea groups are spaced by an alkanediyl linker and which bis-urea moiety is flanked on each side by alkanediyl groups and an oligoethylene glycol or polyethylene glycol group. Such a molecule is a bolaamphiphile, that means a hydrophobic hydrocarbon core with hydrophilic end groups.

As functional component also a betaine may be chosen, preferably a carboxybetaine or sulfobetaine.

Polysaccharides can also be used as functional component, preferably glycosaminoglycanes, for example hyaluronic acid.

In another embodiment the functional component is a polyol, preferably a sugar-derived alcohol, as e.g. sorbitol. The sugar-derived alcohol may be modified. A suitable component comprises a permethylated sorbitol group.

In another embodiment, taurine (2-aminoethanesulfonic acid) is used as functional component.

In another embodiment, the functional component is a zwitterion. A zwitterion is a neutral molecule with a positive and a negative electrical charge, though multiple positive and negative charges can be present.

The disclosure also encompasses functional components which are derivatives comprising a combination of the abovementioned functional groups, e.g. functional components comprising an OEG moiety and a zwitterionic group.

The functional component may comprise one bis-urea moiety or multiple bis-urea moieties. Each bis-urea moiety comprises two urea groups (—NH—C(O)—NH—) connected by a linker. The linker, also referred to as spacer, can be any suitable group, as e.g. an alkanediyl group of 1-12 carbon atoms (—CH2-), e.g. a hexyl or butyl linker, but it can also be an aromatic group.

The functional component (also called filler) interacts and assembles with the thermoplastic elastomer via non-covalent bonds. More specifically, the bis-urea moieties of the elastomer and of the functional component interact which each other, for example via hydrogen bonds. Also the thermoplastic elastomer will self-assemble via the bis-urea moieties. In one embodiment of the blend, the linker between the bis-urea moieties of a functional component and the linker between the bis-urea moieties of the thermoplastic elastomer has the same length. This improves the interaction and matching between the functional component and the thermoplastic elastomer interacting via the urea groups of the bis-urea moieties (also if multiple bis-urea moieties are present). That means that the distance between those groups and moieties in both molecules should be the same. Preferably, the bis-urea moieties of the thermoplastic elastomer and the functional component have the same spacer group between the urea groups, e.g. an identical alkanediyl or aromatic group.

In another embodiment, the linker between the bis-urea moiety of the functional component and the linker between the bis-urea moiety of the thermoplastic elastomer are of different length.

The amount of additive in the blend varies between 0.5-40 wt % based on the mass of the blend, preferably 2-30 wt %, more preferably 3-20 wt %, even more preferably 1-15 wt % or 5-10 wt %.

In one embodiment different functional components are combined in one supramolecular polymer blend.

The functional component that is assembled with the supramolecular thermoplastic elastomer modifies the properties of the supramolecular thermoplastic elastomer. Surprisingly, the blend according to the disclosure shows improved anti-fouling properties and decreased thrombosis when used in an in vivo implant. This also means that the supramolecular polymer blend of the present disclosure has decreased cell-adhesive properties. When used as biomaterial e.g. in shunts, this is expected to increase or prolong the patency of such devices. Surprisingly, the blend according to the disclosure shows improved antifouling properties compared to a bis-urea-modified thermoplastic elastomer without any functional component, and also when compared to the blend of a bisurea-modified thermoplastic elastomer with a bis-urea-modified GRGDS-peptide as known in the art.

The thermoplastic elastomer is a bis-urea functionalized polymer. The thermoplastic elastomer is a segmented polymer of block structure, including soft and hard blocks.

The thermoplastic elastomer has the character of an elastomer material, i.e. a rubbery, plastic material. The thermoplastic elastomer used in the disclosure is different from gels or gel-like polymers.

The hard blocks are (at least partly) crystallized and comprise the bis-urea moiety or moieties. Via the hard block(s), the thermoplastic elastomer reversibly bonds to the functional component and to other molecules of the thermoplastic elastomer, forming reversible cross-links. The hard blocks stiffen the polymer and therefore affect the mechanical properties of the polymer. By changing the ratio between the length of soft and hard blocks the polymer properties may be adjusted.

Preferably, the backbone of the polymer comprises polyether, polyurethane, polyester or polycarbonate blocks. The backbone is the main chain of the polymer and comprises a series of covalently bonded atoms, made up from monomers.

The backbone blocks within the supramolecular thermoplastic elastomer act as soft blocks. Preferably, the polymer backbone is based on polycaprolactone, polylactic acid, polyglycolic acid, polyhydroxybutyrates, polytrimethylene carbonate or a copolymer of any of these.

In one embodiment, the soft block or blocks of the thermoplastic elastomer comprise(s) more than one of said polyether, polyester or polycarbonate blocks, e.g. linked by a poly- or oligoethylene glycol block. For example, polyester and polycarbonate blocks or polyester and polyether blocks may be combined in one thermoplastic elastomer.

Such combinations of different soft block polymers may e.g. result in poly(ester carbonate) elastomers.

In one embodiment the thermoplastic elastomer is a bis-urea functionalized polycaprolactone (PCL-bisurea), e.g. a polymer as depicted in scheme 5 below (indicated as "P"). The synthesis of bis-urea-modified thermoplastic elastomers used in the present disclosure is known. For example, a method for preparing PCL-bisurea can be found in "Biomaterials by the supramolecular control of nanofibers", E. Wisse, ISNB: 978-90-386-1094-8 (PhD thesis, TU Eindhoven) in chapter 2.

The thermoplastic elastomer comprises at least one bis-urea moiety but may also comprise multiple bis-urea moieties.

Preferably, the bis-urea-modified thermoplastic elastomer used in present disclosure does not comprise any UPy moieties.

In one embodiment different thermoplastic elastomers are combined in the supramolecular polymer blend, in combination with one or different functional components.

In a preferred embodiment the supramolecular polymer blend comprises a polycaprolactone-based bis-urea polymer and a bis-urea functionalized functional component which is selected from PEG and OEG.

For example, the supramolecular polymer blend may comprise the following components:

Scheme 1

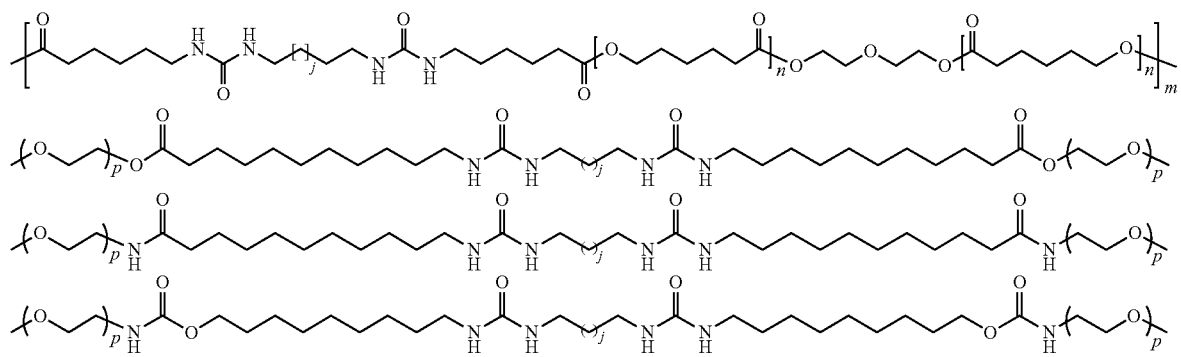

The upper structural formula shows a polycaprolactone bis-urea polymer (PCL-bisurea), the lower ones different functional components based on oligoethylene glycol (OEG-bisurea). The functional groups of each molecule may be coupled via an ester bond, but also via an amide or urethane moiety.

The functional components and the thermoplastic elastomer of the above examples comprise one bis-urea moiety where the urea groups are separated by an alkyl spacer (length indicated with i or j).

For the polymer, n may vary between 5 and 50, m preferably is at least 2.

As explained above, the spacer between the bis-urea moieties may be an oligomer spacer of any suitable length, including alkyls spacers —$(CH_2)_x$—, where x is chosen between 1-14. With reference to the above structural formulas of scheme 1 where the spacer length of the functional component is indicated with "i", where i=2, a butyl spacer is present, where i=4, a hexyl spacer is present. As explained above, in one embodiment the same spacer (also referred to as linker) between bis-urea moieties is used in the polymer and in the functional component. In case of the above depicted PCL-BU polymer (having a spacer length of j=1) a spacer of length i=2 of the functional component would result in good matching of both molecules.

The number of polyethyleneoxide moieties may vary widely, e.g. p as indicated in the formulas above may be 2-50, preferably 5-20.

For example, the polycaprolactone blocks of the PCL-bisurea may have a number average molar mass (Mn) of 1250 or 2000 g/mole. In this embodiment, the thermoplastic elastomer comprises two polycaprolactone blocks (soft blocks) separated by an ethylene glycol group and a chain including the bisurea moiety (hard block).

The oligoethylene blocks of the OEG-bisurea may have a number average molar mass (Mn) between 200 and 800 g/mol, e.g. having a Mn of 350 or 550 g/mole, corresponding to p=6 or 13.

The polymer and the functional component may be monodisperse or polydisperse, i.e. either polymer or oligomer blocks of different length or the same length may be present in the molecules.

Further examples of functional components according to the disclosure are shown below in scheme 2:

Components 1-3 are bis-urea-modified OEG functional components.

Components 4 and 5 of scheme 2 are zwitterionic bis-urea-modified functional components. Components 4 and 5 may be modified such that the carboxyterminal group is replaced by a sulfoxy terminal group. Independently of the terminal group, the number of carbon atoms (indicated as n in scheme 2) between the nitrogen and the terminal group may be varied between 1 and 3 carbon atoms, with 2 carbon atoms being preferred.

Scheme 2

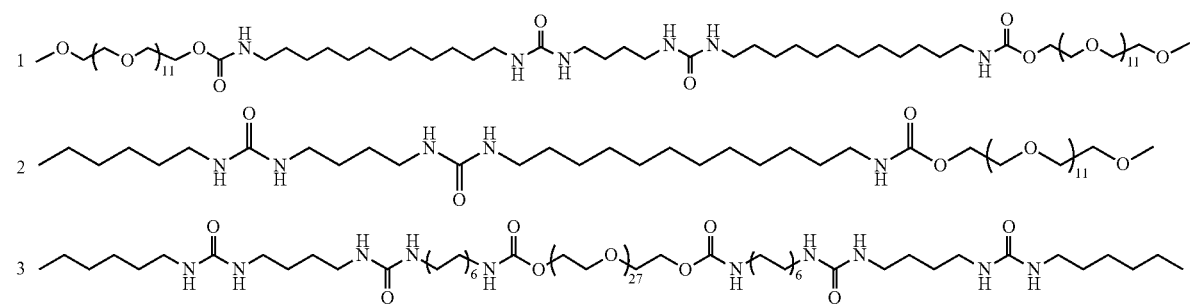

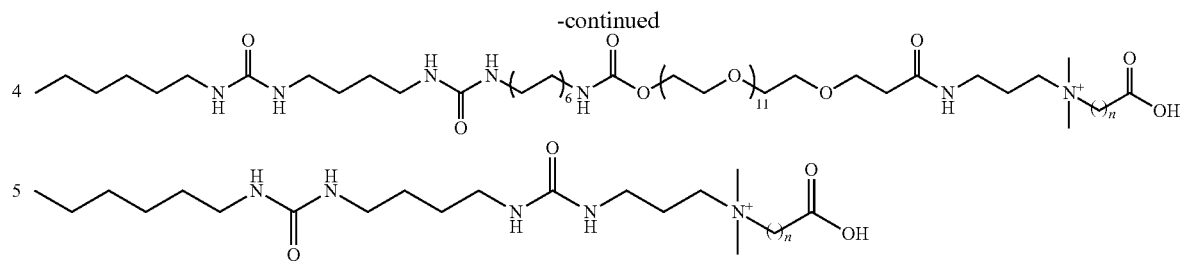

The synthesis of the functional components of the disclosure is known to the person skilled in the art. Exemplatory, the synthesis of components 4 and 5 is described below (indicated as compound 24 in scheme 3 and as compound 19 in scheme 5). The synthesis of components 1-3 is described in detail in the example section.

Component 4 of scheme 2 (designated as C6-U4U-C12-PEG12-C2-tBu or component 24 in scheme 3) may be synthesized according to scheme 3:

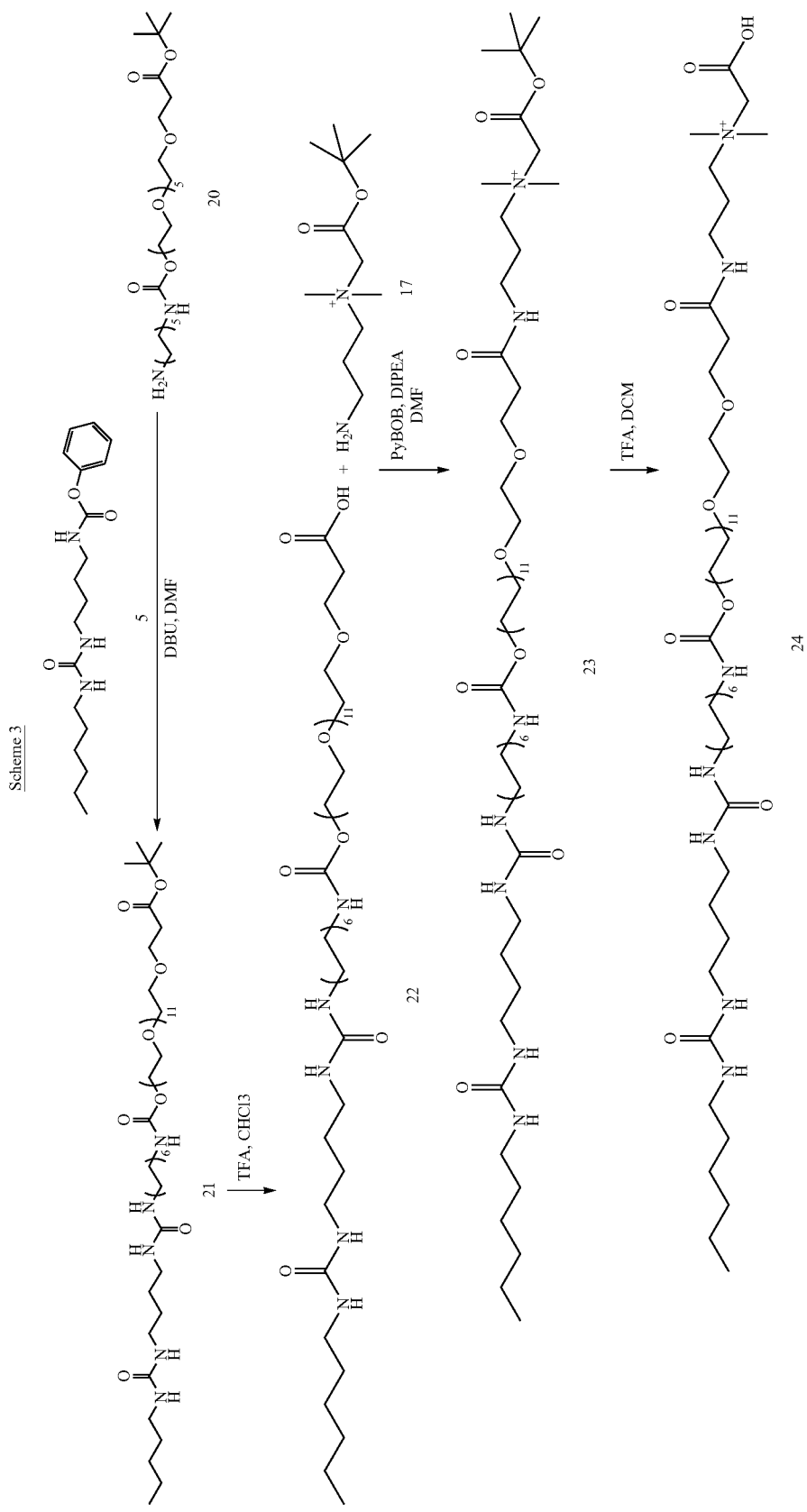

The starting compound 20 (indicated as NH₂-C12-PEG12-C2-tBu, 20) was synthesized as described by de Feijter et al. (Synthetic Letters, 2015, 26, p. 2707-2713).

NH₂-C12-PEG12-C2-tBu 20 (650 mg, 0.72 mmol) and 5 (in scheme 3) (297 mg, 0.89 mmol) were dissolved in 10 mL DMF, followed by the addition of DBU (0.44 mL, 2.89 mmol). The reaction mixture was stirred for 3 hours at 50° C. under Argon. Chloroform (50 mL) was added, the organic phase was washed with 0.5 M citric acid (2×), brine (2×) and dried over Na₂SO₄. The residue was stirred in ether, decanted and dried. Eluting over silica with MeOH/CHCl₃ 4/96 afforded 0.52 g (63%) of the product 21. ¹H-NMR, ¹³C-NMR, FT-IR, and LC-MS were in accordance with the structure.

To a solution of C6-U4U-C12-PEG12-C2-tBu 21 (0.52 g, 0.46 mmol) in DCM (5 mL) TFA (5 mL, 65 mmol) was added and this clear solution was stirred for 1 hour under argon. The solvent was removed under reduced pressure and co-evaporated twice with toluene. Then, ether (15 mL) was added and decanted off (2×). The residue was dissolved in little CHCl₃/MeOH 90/10, precipitated in ether, centrifuged and dried, affording the product 22 (0.40 g, 91%) as a waxy solid. ¹H-NMR, ¹³C-NMR, FT-IR, and LC-MS were in accordance with the structure.

NH₂-C3-tBu-betaine 17 (20.5 mg, 69 µmol), 22 (50.0 mg, 46 µmol) and N,N-diisopropylethylamine (24 µL, 0.138 mmol) were dissolved in DMF/CHCl₃ 5/1 (10 mL). After the addition of PyBOP (28.7 mg, 55 µmol), the solution was stirred at room temperature for 2 h. The solvent was removed under reduced pressure and co-evaporated twice with toluene. Then, ether (15 mL) was added and decanted off (2×). The residue was dissolved in little CHCl₃/MeOH 90/10, precipitated in ether, centrifuged and dried, affording the product 23 (45 mg, 76%) as a white solid. ¹H-NMR, ¹³C-NMR, FT-IR, and LC-MS were in accordance with the structure.

To a suspension of C6-U4U-C12-PEG12-C2-A-C3-tBu-betaine 23 (60 mg, 47 µmol) in DCM (5 mL) TFA (5 mL, 65 mmol) was added and this clear solution was stirred overnight under argon. The solvent was removed under reduced pressure and co-evaporated twice with toluene. Ether (15 mL) was added and decanted off (2×), acetonitril was added, centrifuged and the residue dried. The product 24 (40 mg, 70%). ¹H-NMR, ¹³C-NMR, FT-IR, and LC-MS were in accordance with the structure.

Component 5 of scheme 2 (also designated as C6-U4U-C3-betaine, compound 19) is synthesized according to scheme 4:

Scheme 4

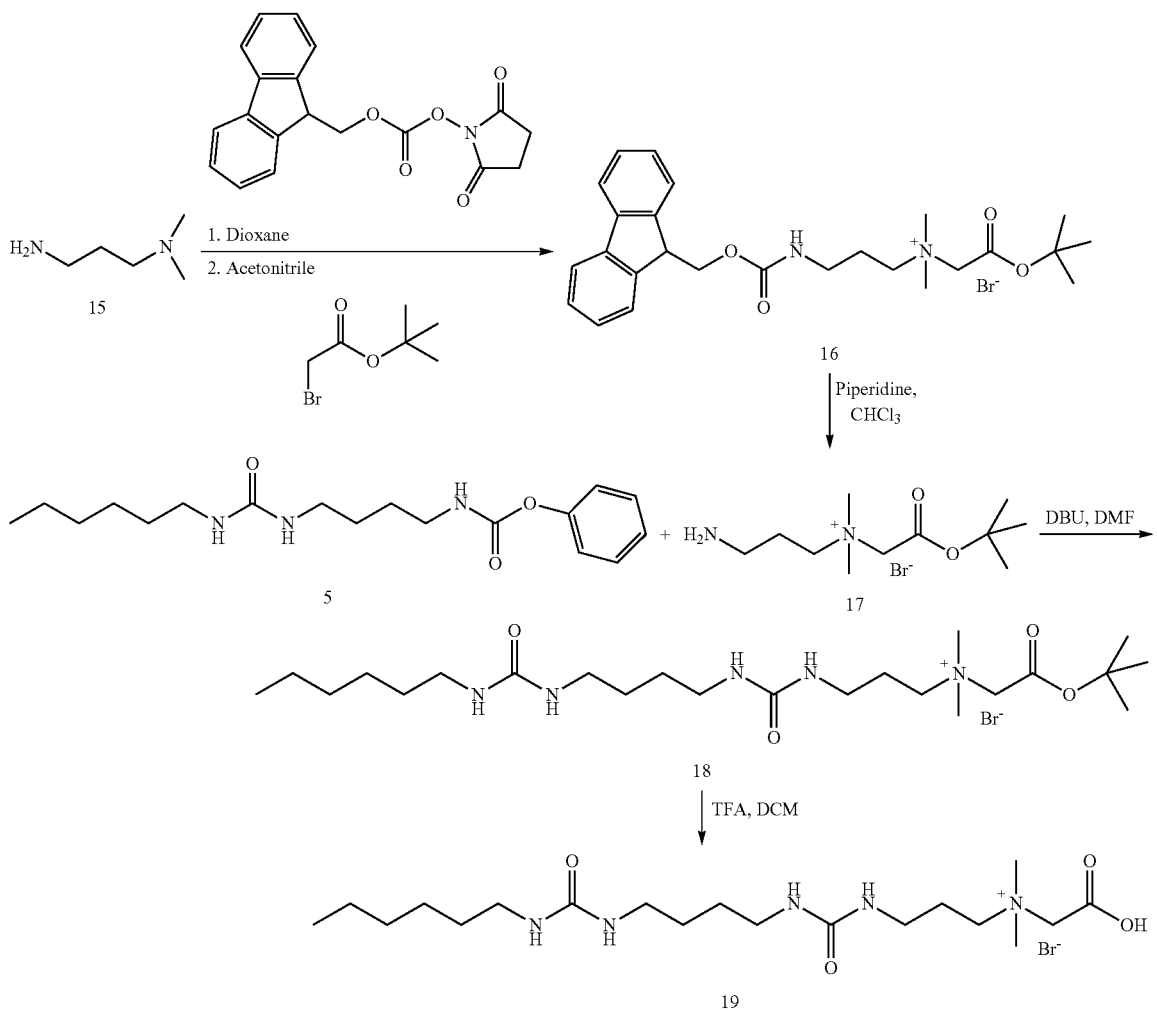

3-(Dimethylamino)-1-propylamine (indicated as 15 in scheme 4), (2.79 mL, 22.2 mmol) was added to a cooled (0° C.) solution of Fmoc N-hydroxysuccinimide ester (5.0 g, 14.8 mmol) in dioxane (20 mL). The solution was stirred for 3 hours at room temperature under argon. The solvent was removed under reduced pressure and the residue was stirred in ether (2×). The combined filtrate was dried under reduced pressure (2.40 g, 7.40 mmol), was dissolved in acetonitrile (5 mL). Tert-butyl 2-bromoacetate (1.58 g, 8.14 mmol) was added. The turbid solution cleared after ~10 minutes and was left stirring over night at room temperature under argon. The solvent was removed under reduced pressure. The residue was stirred twice in ether, decanted off and dried. Eluting over silica with MeOH/CHCl$_3$ 2/98 increasing the polarity to 10/90 afforded 3.81 g (49.6% total yield) of the product 16 as the bromide salt. $^1$H-NMR, $^{13}$C-NMR, FT-IR, and LC-MS were in accordance with the structure.

Fmoc-C3-betaine 16 (3.81 g, 7.33 mmol) was dissolved in chloroform, piperidine (1.13 mL, 0.11 mol) was added. The solution was stirred for 1 hour at room temperature under argon. The solvent was removed under reduced pressure. The residue was stirred twice in ether, decanted off and dried, affording 17 (2.17 g as the bromide salt. $^1$H-NMR, $^{13}$C-NMR, FT-IR, and LC-MS were in accordance with the structure.

NH$_2$-C3-tBu-betaine 17 (192 mg, 0.65 mmol) and 5 (260 mg, 0.78 mmol) were dissolved in 3 mL DMF, followed by the addition of DBU (97 □L, 1.29 mmol). The reaction mixture was stirred for 1 hour at 50° C. under Argon. The solvent was removed under reduced pressure. The residue was stirred in ether, decanted, dissolved in little chloroform, precipitated in ether and decanted, affording 18 (268 mg, 77%) as the bromide salt. $^1$H-NMR, $^{13}$C-NMR, FT-IR, and LC-MS were in accordance with the structure.

C6-U4U-C3-betaine (19): To a suspension of C6-U4U-C3-tBu-betaine 18 (100 mg, 0.186 mmol) in DCM (5 mL) TFA (5 mL, 65 mmol) was added and this clear solution was stirred overnight under argon. The solvent was removed under reduced pressure and co-evaporated twice with toluene. Ether (15 mL) was added and decanted off (2×), and the residue dried, affording 19 (64 mg, 85%) as white solid. $^1$H-NMR, $^{13}$C-NMR, FT-IR, and LC-MS were in accordance with the structure.

The supramolecular polymer blend of the disclosure is suitable as biomaterial, e.g. for use in tissue-engineering and prosthetics and for implants.

The current disclosure also pertains to an implant comprising the supramolecular polymer blend according to the disclosure.

An implant is any article that is inserted in or fixed to a human or animal body. The implant may occur in various form, e.g. in tubular form, as membrane, or as a mesh, depending on its final use.

In one embodiment the implant comprising the supramolecular polymer blend of present disclosure is an in vivo blood contacting device, preferably a cardiovascular or renal device, preferably a cardioprosthetic or nephroprosthetic device, more preferably a vascular graft, cardiac patch, cardiac valve or a kidney membrane. The supramolecular polymer blend of present disclosure is especially suited for arteriovenous shunts.

Implants according to the disclosure are manufactured by mixing the thermoplastic elastomer functionalized with at least one bis-urea moiety with 0.5-40 wt %, preferably 1-15 wt % of the functional component which is functionalized with at least one bis-urea moiety and subsequently processing the mixture. The above described embodiments of the bis-urea-modified thermoplastic elastomer and the bis-urea-modified functional component also apply to the implant comprising the blend of the current disclosure. Different manners of processing are available, including spinning and casting. For example, the bis-urea based thermoplastic elastomer and the functional component may be dissolved in a solvent (e.g. comprising chloroform and methanol), thoroughly mixed (e.g. by sonication) and drop cast. Processing may take place at room temperature. Various spinning methods known to the person skilled in the art can be employed, including electrospinning and solution spinning. Electrospinning is a preferred form of processing, e.g. for manufacture of implants.

The implants are usually multi-layered, comprising at least two layers. The surface layer which is in contact with the body fluids, as e.g. blood, or in contact with the surrounding tissue may be made from the supramolecular polymer blend of present disclosure. In case of a tubular implant, e.g. a graft or shunt, this is the inner layer which is oriented towards the lumen of the implant, and/or the outer layer that is in contact with the surrounding tissue. In case of a heart valve or vascular valve the surface layers that are in contact with blood or surrounding tissue can be composed of this material.

The supramolecular polymer blend of the disclosure results in a layer that has non-fouling properties such that cell adhesion to this layer is minimized, the layer is not overgrown and thrombosis is prevented. This is especially advantageous for vascular implants. Neointimal hyperplasia is prevented or reduced and the patency of the implant is improved and prolonged. Neointimal hyperplasia refers to proliferation and migration of vascular smooth muscle cells primarily in the tunica intima layer of blood vessels, resulting in the thickening of arterial walls and decreased arterial lumen space.

The outer or inner layer(s) of the implant (e.g. radially outward in a tubular graft or in between the surface layers of a valve) are preferably made from a cell-adhesive and optionally bioactive layer to enable tissue formation.

When the implant is a patch, e.g. a cardiac patch or used as kidney membrane the total synthetic scaffold may be made from the supramolecular polymer blend of present disclosure. For example, in case of a bioartificial kidney membrane, the total synthetic scaffold may preferably be made from the polymer blend of current disclosure to prevent clogging of the membrane with proteins. The layer oriented towards the (pre)urine-volume should furthermore be supplemented with cell-adhesive and bioactive properties to promote formation of a tight renal epithelial cell monolayer. The layer oriented toward the blood-volume is, when not covered with endothelial cells, in contact with blood. This requires non-fouling and anti-thrombogenic properties as shown by the supramolecular polymer blend of present disclosure.

It is expected that cardiovascular implants employing the supramolecular polymer blend of the disclosure have improved properties and will therefore increase the life quality of patients, in particular kidney patients requiring hemodialysis which carry AV shunts or grafts comprising the supramolecular polymer blend of current disclosure.

The invention will be further illustrated in the following examples, which do not limit the scope of the invention.

EXAMPLES

The following compounds were used for experiments, the reference numbers and letters of below scheme 5 are used to indicate which functional components were used.

Scheme 5

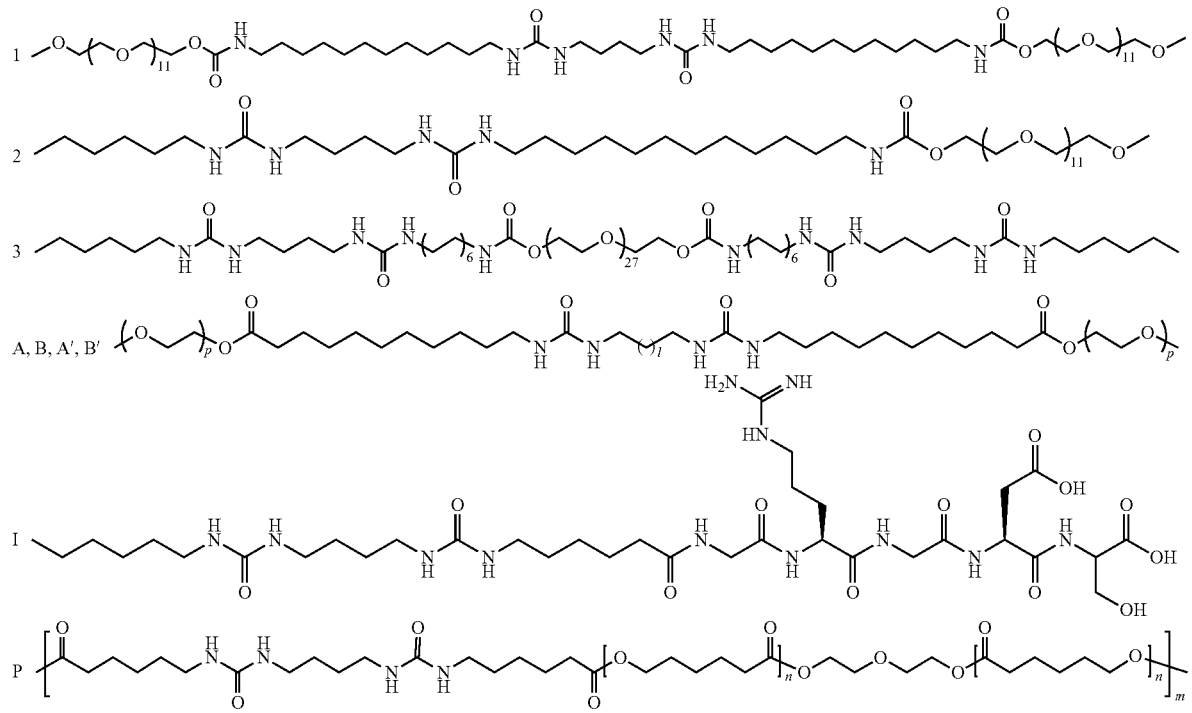

1. Synthesis of Compounds a) Synthesis of PCL-Bisurea (with PCL of Mn=2000, Indicated as "P" in Scheme 5)

Poly(ε-caprolactone) (Mn=2000, 10 g, 5 mmol), N-carbobenzoxy-6-aminohexanoic acid (2.8 g, 11 mmol), 4-(dimethylamino)pyridinium 4-toluenesulfonate (DPTS) (0.7 g, 2.5 mmol), and DCC (3 g, 15 mmol) (all purchased from Acros) were dissolved in CHCl$_3$, and the reaction was allowed to stir for 48 h. The reaction mixture was filtered, and the solvent was evaporated.

The remaining solid material was dissolved in 100 mL of CHCl3 and precipitated in hexane. To remove the remaining DPTS, the product was stirred in MeOH. After removing the MeOH, PCL-bisurea was obtained as a white powder in a 64% yield. A solution of PCL-bisurea (4 g, 1.6 mmol) in 100 mL of EtOAc/MeOH (v/v 2:1) and 400 mg of 10% Pd supported on activated carbon was subjected to hydrogenation under a H2 blanket at room temperature for 4 h. After filtration over Celite, the product was isolated by precipitation in hexane, resulting in compound 2b, as a white powder in a 95% yield. PCL-bisurea (14 g, 6.35 mmol) was dissolved in 100 mL of CHCl3.

b) Synthesis of OEG-Bisurea Functional Components (with OEG of Mn=350 or 550 and Different Spacer Lengths, Indicated as "A", "B", "A'" or "B'" in Scheme 5)

Component A: 350 g/mol of OEG and i=2, resulting in a spacer of four carbon atoms,
Component B: 550 g/mol of OEG and i=2, resulting in a spacer of four carbon atoms,
Component A': 350 g/mol of OEG and i=4, resulting in a spacer of six carbon atoms,
Component B': 550 g/mol of OEG and i=4, resulting in a spacer of six carbon atoms, In a 50 ml two-neck round-bottom flask 3.44 g (11.4 mmol) of N-(tertbutyloxycarbonyl)-11 aminoundecanoic acid, 2.19 g (11.4 mmol) of N-(3-dimethylaminopropyl)-N-ethylcarbodiimide hydrochloride and 1.39 g (11.4 mmol) of dimethylaminopyridine were stirred in 5 ml of dry dichloromethane under argon for 20 min. To the resulting solution was added 2 g (5.7 mmol) of poly (ethylene glycol)-monomethyl ether (Mn ca. 350 or 550) and the reaction mixture was stirred overnight. Purification of the N-(tert-butyloxycarbonyl)-11-aminoundecanoyl-(poly(ethyleneglycol) monomethylether) ester using column chromatography (silica gel, CH2Cl2/Methanol 9:1 v/v) yielded 3.5 g (92%) of transparent oil.

To 30 ml of a 4 M HCl solution in dioxane was added 3 g (4.4 mmol) of N-(tert butyloxycarbonyl)-11-aminoundecanoykpoly(ethyleneglycol)-monomethylether)-ester and the solution was stirred at 0° C. for 1 h and subsequently at room temperature for 2 h. The solvent was evaporated to yield 2.7 g (100%) of the product as its hydrochloric salt, which was used without further purification.

To a solution of 0.70 g (0.43 mmol) of 1,4-diisocyanatobutane (or 1,6-Diisocyanatohexane) in 2 ml of dichloromethane, solution of 11-aminoundecanoyl-(poly(ethylene glycol)-monomethylether)-ester (0.55 g, 0.86 mmol) and triethylamine (0.23 ml, 2.5 mmol) in 2 ml dichloromethane was added and stirred overnight. The solution was concentrated and the product was purified using column chromatography (silica gel, CHCl3/Methanol 19:1 v/v). Finally, precipitation from diethyl ether yielded 0.40 g (71%) of the product as a white solid.

c) Synthesis of OEG-Bisurea Functional Component (mPEG12-C12)2-U4U (Indicated as Component 1 in Scheme 5)

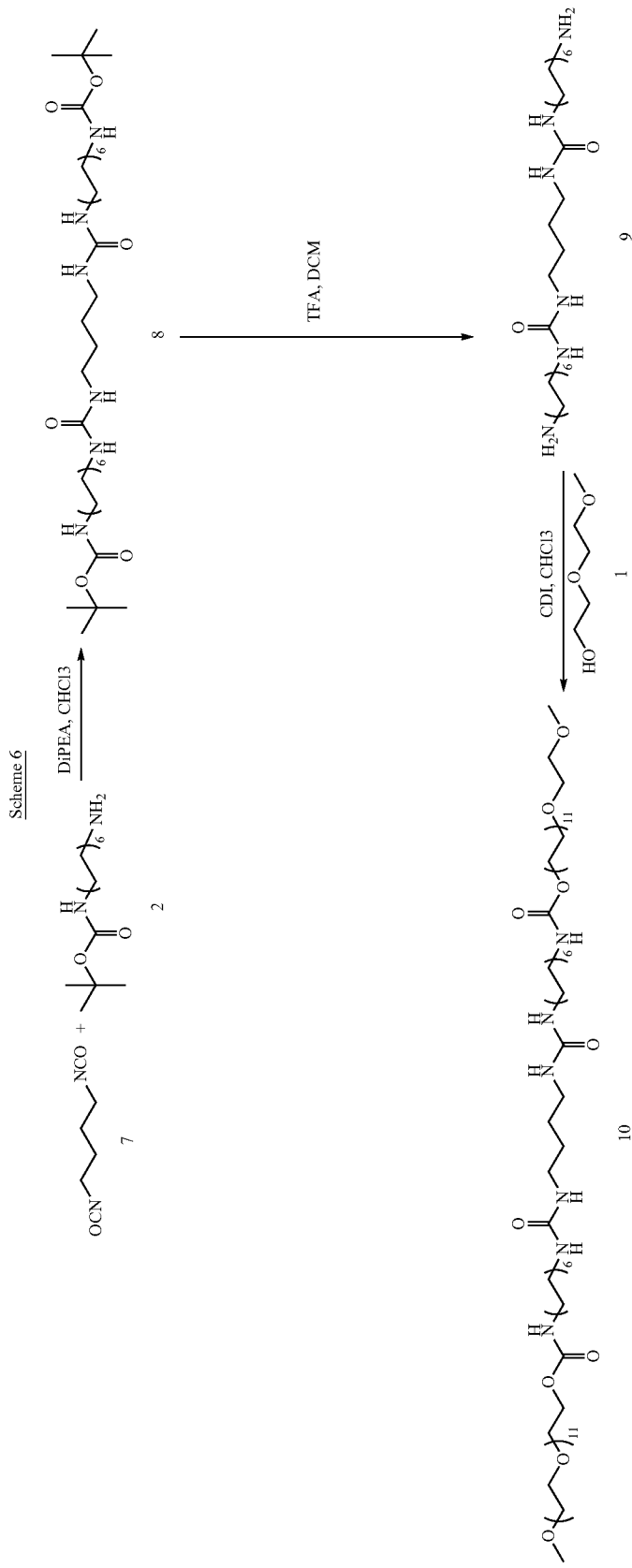

To a solution of 1,4-diisocyanatobutane 7 (0.2 g, 1.43 mmol) and DiPEA (0.75 mL, 4.28 mmol) in $CHCl_3$ (10 mL), tert-butyl (12-aminododecyl)carbamate 2 (0.86 g, 2.85 mmol) in 5 mL $CHCl_3$ was added. The reaction mixture was stirred for 3 hours at room temperature under Argon. The solvent was removed under reduced pressure and subsequently, stirred in acetonitrile, sonicated, and centrifuged (3×). Resulting in an off-white solid 8 (0.85 g, 80%). $^1$H-NMR, $^{13}$C-NMR, FT-IR, and MALDI-TOF MS were in accordance with the structure.

To a suspension of (N-Boc-C12)2-U4U 8 (0.85 g, 1.15 mmol) in DCM (5 mL) TFA (5 mL, 65 mmol) was added and this clear solution was stirred for 1 hour under argon. The solvent was removed under reduced pressure and co-evaporated twice with toluene. Then, ether (15 mL) was added and decanted off (2×). The product 9 (0.80 g, 91%) was isolated as the TFA-salt. $^1$H-NMR, $^{13}$C-NMR, FT-IR, and LC-MS were in accordance with the structure.

MPEG12 1 (1.04 g, 1.85 mmol) in chloroform (10 mL) was added dropwise to a solution of CDI (0.32 g, 1.96 mmol) in 15 mL chloroform. After stirring for 3 hours, ($NH_2$—C12-)2-U4U 9 (0.71 g, 0.93 mmol) was added. The reaction mixture was stirred for 2 days at room temperature under Argon. Then overnight at 80° C., after which the solvent was removed in vacuo. The residue was dissolved in little $CHCl_3$/MeOH 90/10 and precipitated in ether and filtered (2×). Eluting over silica with MeOH/$CHCl_3$ 10/90 afforded 1.2 g (76%) of the pure product 10. $^1$H-NMR, $^{13}$C-NMR, FT-IR, and MALDI-TOF MS were in accordance with the structure.

d) Synthesis of OEG-Bisurea Functional Component C6-U4U-C12-mPEG12 (Indicated as Compound 2 in Scheme 5)

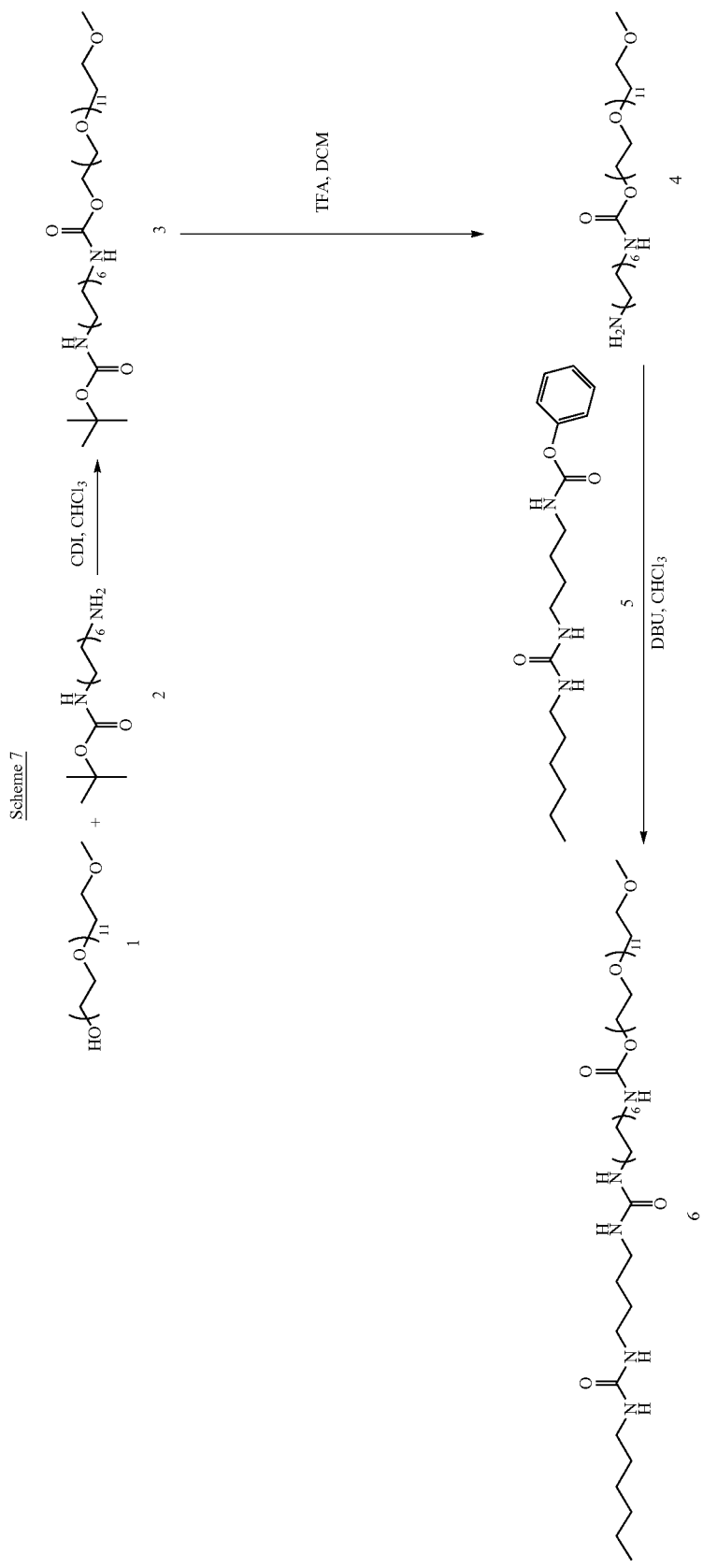

MPEG12 1 (1.0 g, 1.78 mmol) in chloroform (10 mL) was added dropwise to a solution of CDI (0.32 g, 1.96 mmol) in 15 mL chloroform. After stirring for 3 hours, tert-butyl (12-aminododecyl)carbamate 2 (0.59 g, 1.96 mmol) was added. The reaction mixture was stirred for 24 hours, after which the solvent was removed in vacua, Eluting over silica with MeOH/monoglyme/EtOAc 1/5/20 afforded 1.5 g (95%) of the product 3 as the imidazole salt. $^1$H-NMR, $^{13}$C-NMR, FT-IR, and LC-MS were in accordance with the structure.

To a solution of N-Boc-C12-mPEG12 3 (1.5 g, 1.69 mmol) in DCM (6 mL) TFA (6 mL, 78 mmol) was added and this solution was stirred for 1 hour under argon. The solvent was removed under reduced pressure and co-evaporated twice with toluene. Then, ether (15 mL) was added and decanted off (2×), resulting in an oil that solidified upon standing. The product 4 (1.5 g, quant) was isolated as the TFA-salt. $^1$H-NMR, $^{13}$C-NMR, FT-IR, and LC-MS were in accordance with the structure.

1,4-Butanediisocyanate (2.0 g, 14.3 mmol) and phenol (1.34 g, 14.3 mmol) were dissolved in DCM (40 mL) and DiPEA (5.0 mL, 28.5 mmol) was added. After stirring for 2 hours, Hexylamine (1.92 mL, mmol) was added to the slurry. The reaction mixture was stirred for 24 hours, after which the solvent was removed in vacuo. Eluting over silica with CHCl$_3$/MeOH 97/3 afforded 1.6 g (33%) of the pure product 5. $^1$H-NMR, $^{13}$C-NMR, FT-IR, and LC-MS were in accordance with the structure.

12-Aminododecyl-mPEG12 4 (0.86 g, 0.95 mmol) and 5 (0.35 g, 1.04 mmol) were dissolved in 10 mL DMF, followed by the addition of DBU (0.57 mL, 3.78 mmol). The reaction mixture was stirred for 4 hours at 50° C. under Argon. The solvent was removed under reduced pressure and co-evaporated twice with toluene. The residue was stirred in 15 mL ether (2×) and 15 mL acetonitrile (2×), dissolved in little CHCl$_3$/MeOH 90/10 and precipitated in ether/acetic acid 95/5. The solid was filtered off and dried in vacua, yielding an off-white solid 6 (0.5 g, 51%). $^1$H-NMR, $^{13}$C-NMR, FT-IR, and MALDI-TOF MS were in accordance with the structure.

e) Synthesis of OEG-Bisurea Functional Component (C6-U4U-C12)2-PEG28 (Indicated as Compound 3 in Scheme 5)

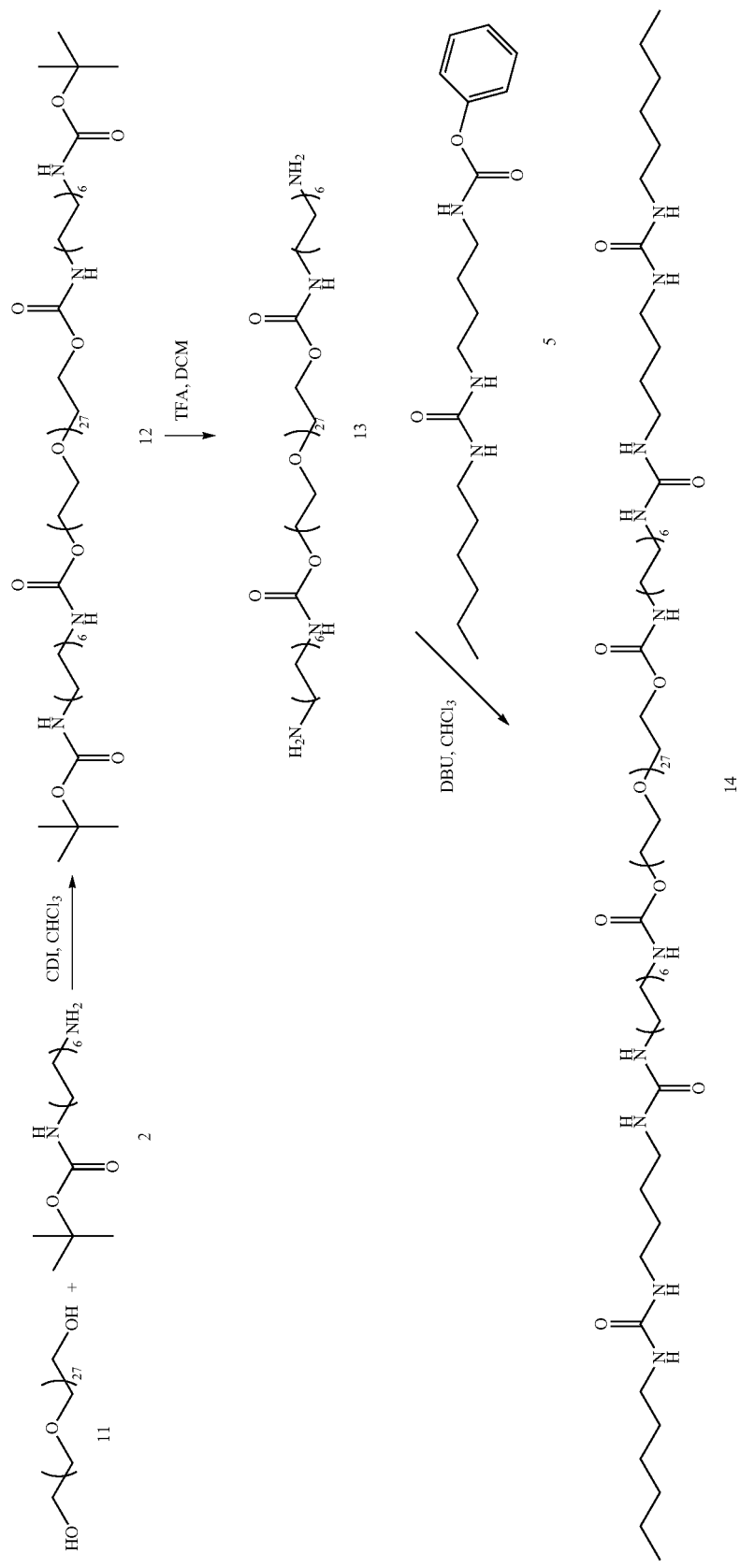

PEG28 11 (0.70 g, 0.56 mmol) in chloroform (5 mL) was added dropwise to a solution of CDI (0.20 g, 1.23 mmol) in 10 mL chloroform. After stirring for 4 hours, tert-butyl (12-aminododecyl)carbamate 2 (0.44 g, 1.64 mmol) was added. The reaction mixture was stirred for 3 days at room temperature under Argon. Then overnight at 80° C., after which the solvent was removed in vacuo. The residue was dissolved in little $CHCl_3$/MeOH 90/10 and precipitated in ether and filtered (2×). Eluting over silica with MeOH/$CHCl_3$ 5/95 afforded 0.89 g (84%) of the pure product 12. $_1$H-NMR, $^{13}$C-NMR, FT-IR, and MALDI-TOF MS were in accordance with the structure.

To a suspension of $(NH_2—C12)_2$-PEG28 12 (0.89 g, 1.15 mmol) in DCM (10 mL) TFA (4 mL, 65 mmol) was added and this clear solution was stirred for 1 hour under argon. The solvent was removed under reduced pressure and co-evaporated twice with toluene. Then, ether (15 mL) was added and decanted off (2×). The product 13 (0.90 g, quant) was isolated as the TFA-salt. $^1$H-NMR, $^{13}$C-NMR, FT-IR, and LC-MS were in accordance with the structure.

$(NH_2$—C12-$)_2$-PEG28 13 (0.90 g, 0.53 mmol) and 5 (0.39 g, 1.16 mmol) were dissolved in 10 mL $CHCl_3$, followed by the addition of DBU (0.63 mL, 4.20 mmol). The reaction mixture was stirred for 24 hours at 50° C. under Argon. Then, 50 mL $CHCl_3$/MeOH 90/10 were added, the organic phase was washed with 0.5 M citric acid and brine and dried over $Na_2SO_4$. The residue was stirred in 15 mL ether (2×) and 15 mL acetonitrile (2×), dissolved in little $CHCl_3$/MeOH 90/10 and precipitated in ether/acetic acid 95/5. The solid was filtered off and dried in vacuo, yielding an off-white solid 14 (0.9 g, 78%). $^1$H-NMR, $^{13}$C-NMR, FT-IR, and MALDI-TOF MS were in accordance with the structure.

f) Synthesis of GRGDS-Bisurea (Indicated as "I" in Scheme 5)

Synthesis of this compound has been disclosed in Wisse et al. (Biomacromolecules 2006, 7, p. 3385-3395).

2. Synthesis of Supramolecular Polymer Blends

Supramolecular polymer blends according to the disclosure comprising PCL-bisurea as thermoplastic elastomer (indicated as P in scheme 5) and one of the various OEG-bisurea (indicated as 1, 2, 3, A, A', B, B' in scheme 5) as functional component were prepared. For comparison to the prior art polymer blends, a blend comprising the same polymer P and a bisurea-functionalized GRGDS peptide (I) was also prepared. Varying amounts of these components were combined (see Tables 1 and 2).

For the experiments the respective amounts of thermoplastic elastomers and functional component were dissolved in a solvent comprising a mixture of chloroform and methanol (9:1), sonicated for 10 min, and drop cast at room temperature to obtain films. Films were dried at room temperature for 4 hours, and further dried under vacuum overnight.

Figure 4A:
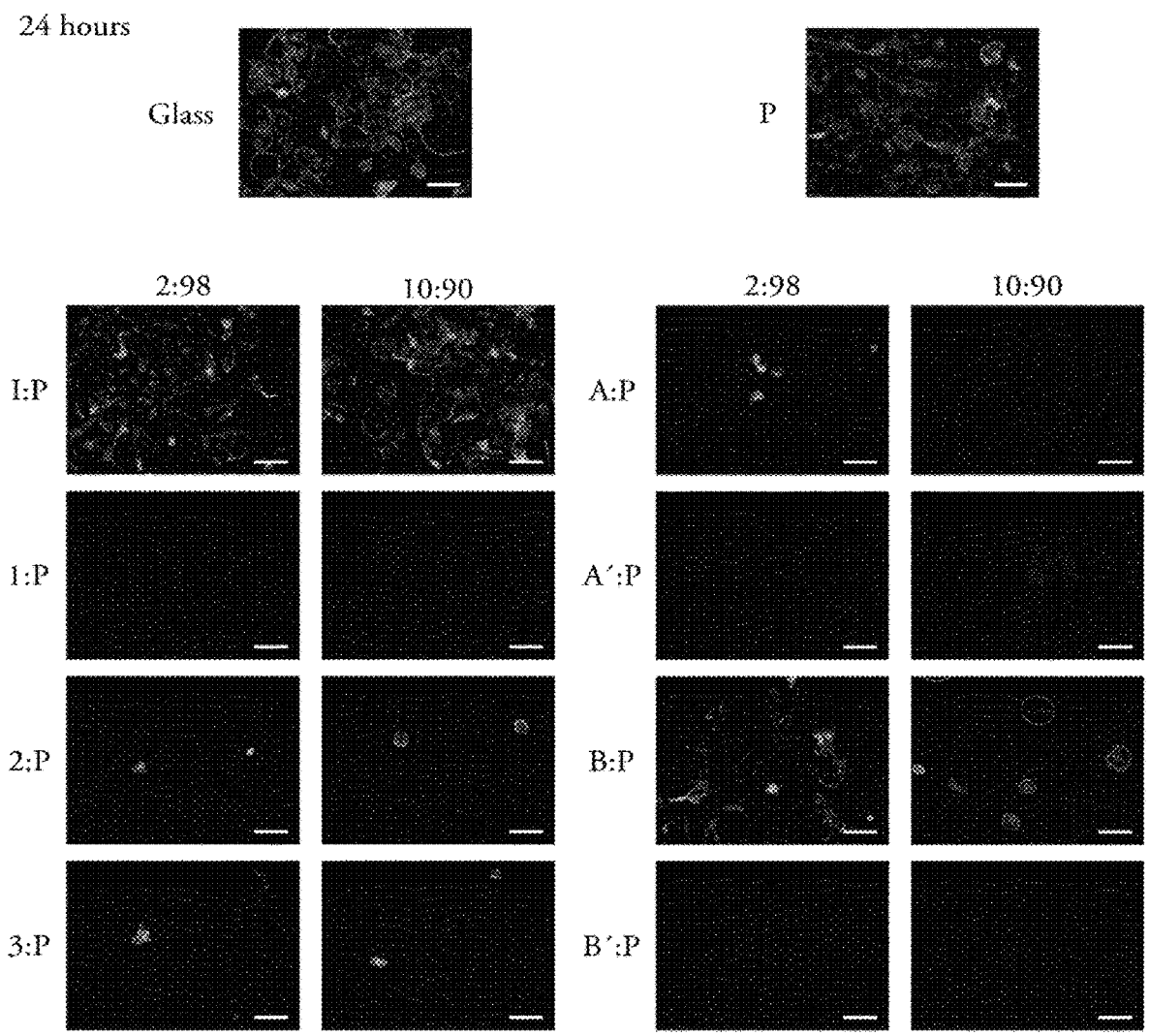
FIGS. 4A-B also show the cell adhesion behavior of HK2 cells at 24 and 72 hours after seeding on different surfaces.
Figure 4B:
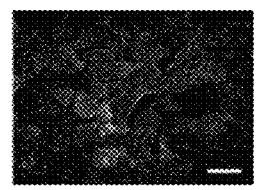
Figure 4B:
Figure 4B:
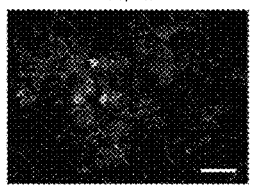
Figure 4B:
Figure 4B:
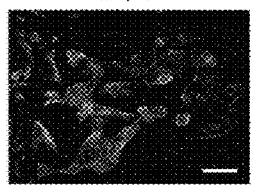
Figure 4B:
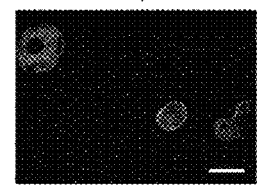
Figure 4B:
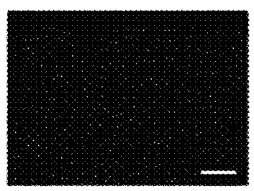
Figure 4B:
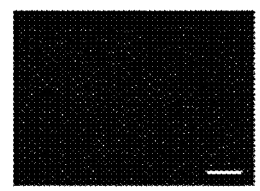
Figure 4B:
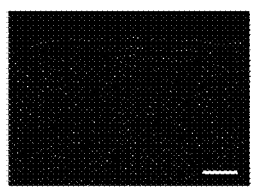
Figure 4B:
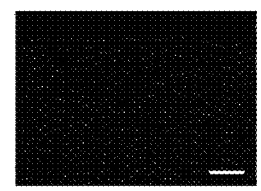
Figure 4B:
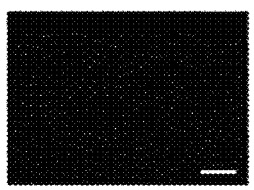
Figure 4B:
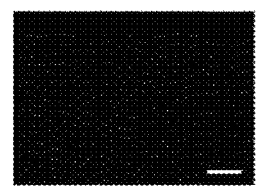
Figure 4B:
Figure 4B:
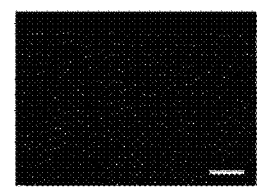
Figure 4B:
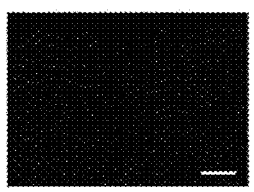
Figure 4B:
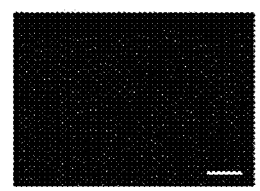
Figure 4B:
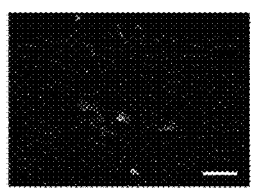
Figure 4B:
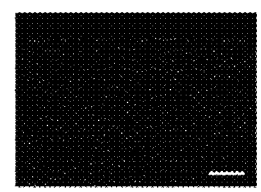

For the cell adhesion studies presented in FIGS. 4A-B, non-adhesive surfaces were also prepared by drop-cast procedure. To this end, each of the described compounds was dissolved in hexa-fluoroisopropanol (HFIP) in the presence of polymer P, resulting in a viscous polymer solution. Subsequently, a drop cast polymer surface was prepared by applying 50 μL onto a glass slide, followed by overnight incubation in vacuo to remove the HFIP solvent traces.

TABLE 1 composition of films comprising the supramolecular polymer blend of films used for experiments

| | Polymer P (wt %) | | | | |
| --- | --- | --- | --- | --- | --- |
| | 100 | 98 | 95 | 90 | 85 |
| Functional component A or B (as indicated) (wt %) | 0 | 2 | 5 | 10 | 15 |

TABLE 2 composition of films comprising the supramolecular polymer blend of films used for experiments

| | Polymer P (wt %) | | |
| --- | --- | --- | --- |
| | 100 | 98 | 90 |
| Functional component 1, 2, 3, A, A', B, B' or I (as indicated) (wt %) | 0 | 2 | 10 |

3. Test Methods a) Water Contact Angle (WCA) Measurement

Water contact angle measurements were performed using an OCA30 contact angle system from DataPhysics, and SCA20 software was used for analysis. 5 μL water droplets with a dosing rate of 1 μL/min were dropped onto films. Contact angles were measured at the polymer-air-water interface immediately.

b) Resazurin Assay

This assay measures the total mitochondrial activity in a cell culture and indicates cell viability.

Non-fluorescent resazurin was added to the culture medium of HK-2 (human kidney) cells, which were cultured on different films comprising the supramolecular polymer blend of current disclosure or only the base polymer (00: 100). As polymer blend a combination of polymer P with functional component A or B was chosen (as shown in Table 1). The non-fluorescent resazurin is taken up and metabolized to fluorescent resazurin by viable cells. The fluorescent resazurin is excreted into the culture media. Subsequently, the fluorescence intensity of the culture medium was measured (in AU) after 3, 24 and 72 hours to indicate the extent of cell viability.

c) Cell Adhesion on Supramolecular Polymer Blends of the Disclosure

Immortalized human proximal tubular kidney epithelial cells (HK-2) were seeded on different films comprising the supramolecular polymer blend of current disclosure. Cells were seeded at a density of $1.5 \times 10^4$ HK-2/cm$^2$ and maintained under standard culturing conditions (DMEM supplemented with 10 vol % fetal bovine serum and 1 vol % Penicillin/Streptomycin; 5% $CO_2$ at 37° C.).

Polymer blends were prepared as described above with varying amounts of thermoplastic elastomer (P) and functional component (as shown in Tables 1 and 2). As control, cells were also seeded on bare glass and on a film made from the base polymer alone (00:100).

Non-adhesive properties of the different surfaces were evaluated for one set of data at 3 hours, 24 hours and 72 hours, and for another set of data at 24 and 72 hours through evaluation of the cytoskeletal organization in adhered cells.

To this end fluorescent phalloidin staining was performed to identify actin filaments of the cytoskeleton, indicative for the adhesion and spreading of HK-2 cell on the tested surfaces. Non-nouling surfaces prevent the adhesion of cells that is manifested by the absence or impairment of mature actin-filament formation in the few receding cells.

4. Properties of Supramolecular Polymer Blends

FIG. 1 shows the water contact angle of different supramolecular polymer blends according to the disclosure, comprising different amounts of functional component of different molecular weight (A or B, as indicated in scheme 5 and FIG. 1) in comparison to the supramolecular base polymer (P) without any functional component (00:100).

With increasing amounts of functional component the water contact angle of the surfaces decreases, indicating a more hydrophilic surface of the polymer blends according to the disclosure.

Figure 2:
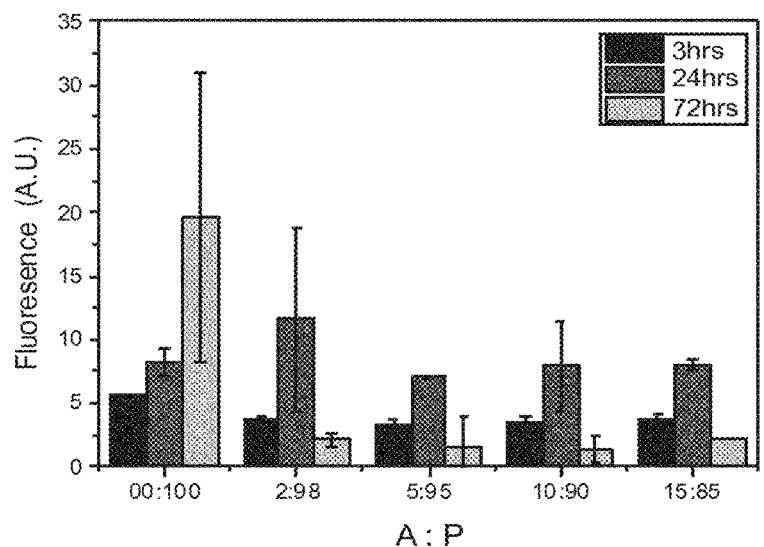
FIG. 2 shows the results of Resazurin assays.
Figure 2:
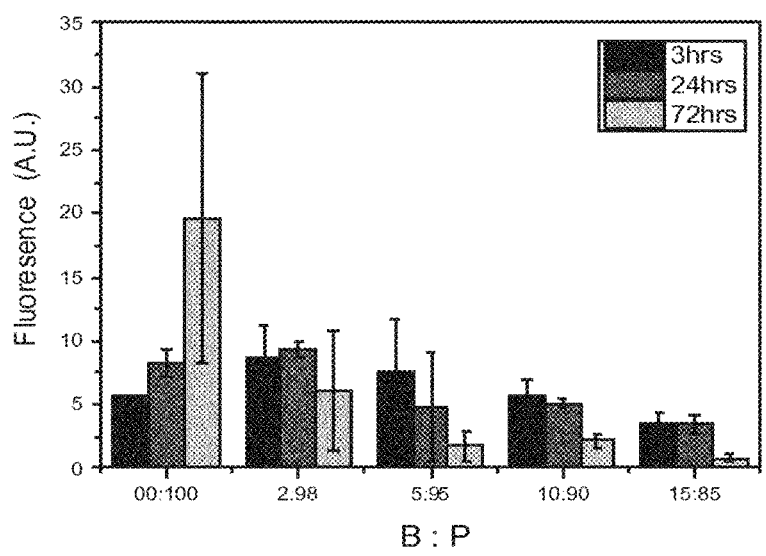

FIG. 2 shows the results of Resazurin assays.

Especially after 72 hours of cell culturing on the different blends and the control surfaces (polymer P without functional component, indicated as 00:100) the effect is visible: a much lower fluorescence signal is measured for the blends of the disclosure than for the control surfaces, reflecting the reduced number of adhered cells on these blends. This will prevent cell growth on the surface of materials comprising the supramolecular polymer blend of present disclosure and therefore reduce fouling of such surfaces.

FIGS. 3A-1, 3A-2, 3B-1, 3B-2, 3C-1 and 3C-2 show the cell adhesion behavior of HK2 cells at different times after seeding on different surfaces.

Figures 1, 3B:
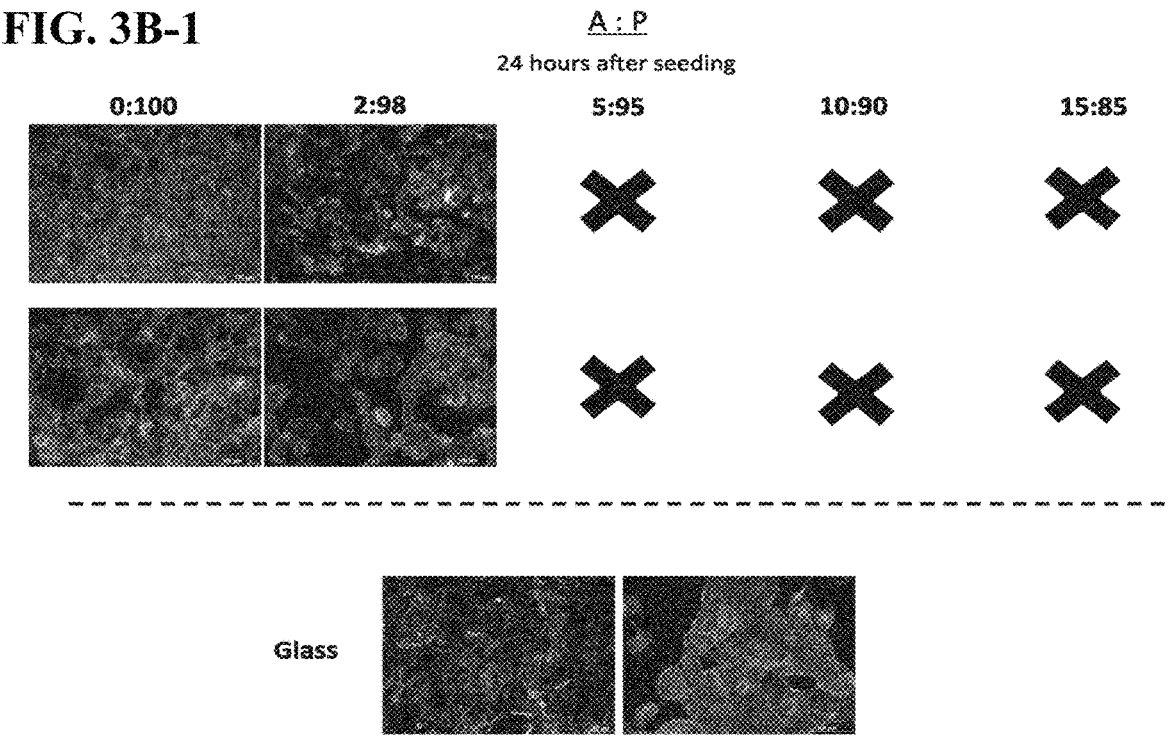
Figures 2, 3B:
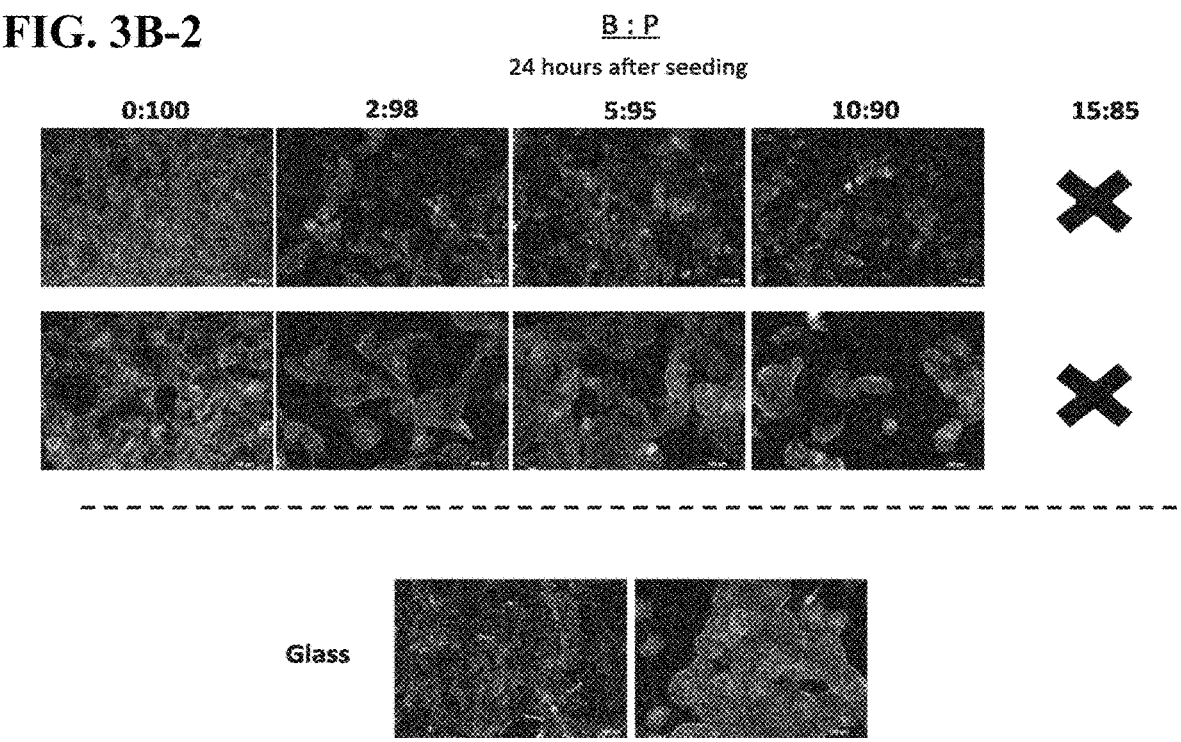
Figures 1, 3C:
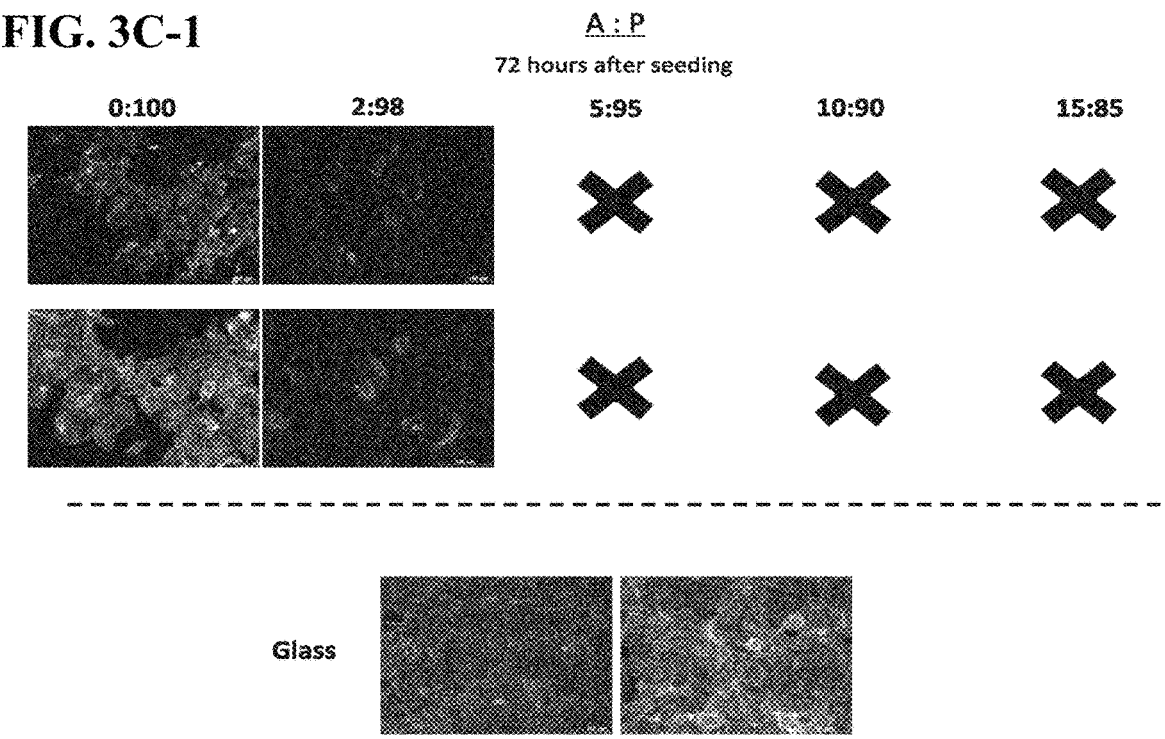
Figures 2, 3C:
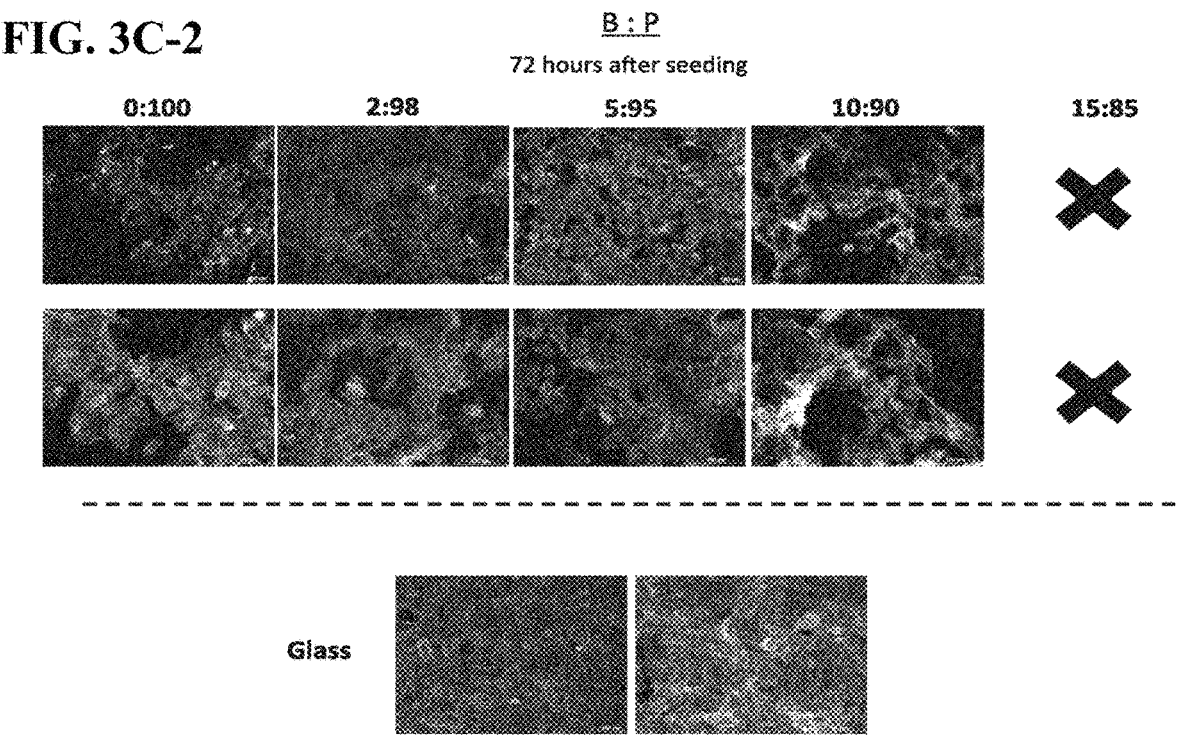

FIGS. 3A-1 and 3A-2 show cell adhesion 3 hours after seeding, FIGS. 3B-1 and 3B-2 24 hours after seeding and FIGS. 3C-1 and 3C-2 after 72 hours.

The panels are separated into two parts. FIGS. 3A-1, 3B-1 and 3C-1 show films of polymer blends comprising base polymer P and A as functional component, while FIGS. 3A-2, 3B-2 and 3C-2 show the same results for a polymer blend including functional component B. The panels include up to 4 different polymer blends according to the disclosure with different ratios of functional components A or B to base polymer (2:98, 5:95, 10:90 and 15:85). Also included are two controls: cells seeded on a bare glass surface and cells seeded on a film made from the base polymer without any filler (00:100).

The experimental data indicate that less cell adhesion occurs on the polymer blends according to the disclosure compared to a base polymer without a functional filler.

FIGS. 4A-B also show the cell adhesion behavior of HK2 cells at 24 and 72 hours after seeding on different surfaces. Polymer blends were prepared at two different weight ratios of the functional component to base polymer P (2:98 and 10:90). FIG. 4A shows cell adhesion after 24 hours on surfaces comprising the base polymer P blended with one of the described functional components 1, 2, 3, A, A', B or B'. 4B shows cell adhesion after 72 hours on the same polymer blend surfaces as shown in FIG. 4A. Non-adhesive behavior of the polymer surfaces blended with the described functional components were compared to a glass surface, compared to the pristine base polymer P, and compared to the prior art polymer blend comprising polymer P and the functional component I. All blends according to the disclosure at all time points after seeding show less cell adhesion (i.e. less attached cells) compared to a glass surface, compared to the surface of the polymer P without functional component and compared to the prior art polymer blend comprising bisurea-functionalized GRGDS-peptide (functional component I). Therefore, the data show that addition of the described functional components comprising one bis-urea moiety or multiple bisurea moieties to a elastomeric bisurea base polymer prevents cell adhesion to these polymer blend surfaces. Thus, the functional components described in the disclosure add anti-fouling surface properties to the bis-urea base polymer, whereas the bisurea-functionalized GRGDS-peptide (functional component I) that is indicated as prior art does not possess these non-adhesive properties.

The invention claimed is:

1. A supramolecular polymer blend comprising:
   a thermoplastic elastomer functionalized with at least one bis-urea moiety, and
   a functional component which is functionalized with at least one bis-urea moiety having a linker on each side of their respective urea groups, wherein the linker is a C1 to C12 group,
   wherein the functional component is present in an amount of 0.5-40 wt % based on a total mass of the polymer blend and
   wherein the functional component is selected from the group consisting of polyalkylene glycol, betaine, polysaccharide, zwitterion, polyol, and taurine.

2. The supramolecular polymer blend according to claim 1 wherein the polyalkylene glycol is an oligoethylene glycol or a polyethylene glycol.

3. The supramolecular polymer blend according to claim 1 wherein the betaine is a carboxybetaine or sulfobetaine.

4. The supramolecular polymer blend according to claim 1 wherein the polysaccharide is a glycosaminoglycane.

5. The supramolecular polymer blend according to claim 1 wherein the polyol is a sugar-derived alcohol.

6. The supramolecular polymer blend according to claim 1 wherein the thermoplastic elastomer functionalized with at least one bis-urea moiety has a backbone comprising a polyether, polyester or polycarbonate, or a copolymer of any of these.

7. An implant comprising the supramolecular polymer blend according to claim 1.

8. The implant according to claim 7 which is an in vivo blood contacting device.

9. A process to manufacture an implant comprising the supramolecular polymer blend of claim 1, comprising the steps of:
   mixing 0.5-40 wt % of the functional component with the thermoplastic elastomer, and
   processing the blend by spinning or casting.

10. The supramolecular polymer blend according to claim 1 wherein the polysaccharide is hyaluronic acid.

11. The supramolecular polymer blend according to claim 1 wherein the polyol is sorbitol.

12. The supramolecular polymer blend according to claim 1 wherein the polyol is permethylated sorbitol.

13. The supramolecular polymer blend according to claim 1 wherein the thermoplastic elastomer functionalized with at least one bis-urea moiety has a backbone comprising poly (trimethylene carbonate), polyglycolic acid, polyhydroxybutyrates, polycaprolactone, polylactic acid, or a copolymer of any of these.

14. The implant according to claim 7 which is an in vivo blood contacting device selected from the group consisting of cardiovascular and renal devices.

15. The implant according to claim 7 which is an in vivo blood contacting device selected from the group consisting of cardioprosthetic and nephroprosthetic devices.

16. The implant according to claim 7 which is an in vivo blood contacting device selected from the group consisting of vascular grafts, cardiac patches, cardiac valves, vascular valves, and kidney membranes.

17. A process to manufacture an implant comprising the supramolecular polymer blend of claim 1, comprising the steps of:

mixing 0.5-40 wt % of the functional component with the thermoplastic elastomer, and processing the blend by electro-spinning.

\* \* \* \* \*